(12) United States Patent
He et al.

(10) Patent No.: US 11,717,163 B2
(45) Date of Patent: Aug. 8, 2023

(54) WEARABLE DEVICE, SIGNAL PROCESSING METHOD AND DEVICE

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Huidong He, Beijing (CN); Hao Zhang, Beijing (CN); Lili Chen, Beijing (CN); Yu Lei, Beijing (CN); Peng Han, Beijing (CN); Yuanjie Lu, Beijing (CN); Yukun Sun, Beijing (CN); Qingwen Fan, Beijing (CN); Shuo Zhang, Beijing (CN); Yachong Xue, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 657 days.

(21) Appl. No.: 16/549,071

(22) Filed: Aug. 23, 2019

(65) Prior Publication Data
US 2020/0237221 A1 Jul. 30, 2020

(30) Foreign Application Priority Data
Jan. 29, 2019 (CN) .......................... 201910086054.7

(51) Int. Cl.
*A61B 5/00* (2006.01)
*A61B 5/369* (2021.01)
*G06F 1/16* (2006.01)

(52) U.S. Cl.
CPC ............ *A61B 5/0004* (2013.01); *A61B 5/369* (2021.01); *A61B 5/6803* (2013.01); *G06F 1/163* (2013.01)

(58) Field of Classification Search
CPC ... A61B 5/0004; A61B 5/0006; A61B 5/0002; A61B 5/0015; A61B 5/0017;
(Continued)

(56) References Cited

U.S. PATENT DOCUMENTS

2017/0035317 A1* 2/2017 Jung ..................... A61B 3/0025
2017/0143226 A1* 5/2017 Ding ..................... A61B 5/397
(Continued)

FOREIGN PATENT DOCUMENTS

CN 102419588 A 4/2012
CN 103150023 A 6/2013
(Continued)

OTHER PUBLICATIONS

Zhongke et al. CN 108433722, English translation provided by Espacenet (Year: 2018).*
(Continued)

*Primary Examiner* — Andrey Shostak
(74) *Attorney, Agent, or Firm* — Kinney & Lange, P.A.

(57) ABSTRACT

A wearable device, a signal processing method and a signal processing device are disclosed. The wearable device includes a processor and a signal collector electrically connected to the processor. The signal collector includes at least one electroencephalogram sensor configured to collect an electroencephalogram signal and at least one electrooculogram sensor configured to collect an electrooculogram signal. The processor is configured to generate a control signal based on the electroencephalogram signal and the electrooculogram signal, and the electroencephalogram sensor and the electrooculogram sensor are different sensors.

18 Claims, 3 Drawing Sheets

(58) Field of Classification Search
CPC ......... A61B 5/369; A61B 5/372; A61B 5/374; A61B 5/375; A61B 5/377; A61B 5/6801; A61B 5/6802; A61B 5/6803; A61B 5/68; A61B 5/378; A61B 5/398; G06F 1/163; G06F 3/015

See application file for complete search history.

(56) References Cited

U.S. PATENT DOCUMENTS

| | | | |
|---|---|---|---|
| 2017/0150898 A1* | 6/2017 | Liu | A61B 5/398 |
| 2018/0103917 A1* | 4/2018 | Kim | A61B 5/291 |
| 2018/0224936 A1 | 8/2018 | Tumey | |
| 2019/0073605 A1* | 3/2019 | Keller | A61B 5/316 |
| 2019/0121431 A1* | 4/2019 | Lee | G06F 3/011 |
| 2019/0369727 A1* | 12/2019 | Li | A61B 5/316 |
| 2020/0260962 A1* | 8/2020 | Mouchantaf | A61B 5/4809 |

FOREIGN PATENT DOCUMENTS

| | | |
|---|---|---|
| CN | 103338265 A | 10/2013 |
| CN | 104360730 A | 2/2015 |
| CN | 104820500 A | 8/2015 |
| CN | 105487676 A | 4/2016 |
| CN | 106339091 A | 1/2017 |
| CN | 107037883 A | 8/2017 |
| CN | 107483992 A | 12/2017 |
| CN | 108433722 A | 8/2018 |
| CN | 108681391 A | 10/2018 |
| KR | 20120109160 A | 10/2012 |

OTHER PUBLICATIONS

First Chinese Office Action dated Mar. 22, 2021, received for corresponding Chinese Application No. 201910086054.7, 25 pages.

* cited by examiner

WEARABLE DEVICE, SIGNAL PROCESSING METHOD AND DEVICE

CROSS-REFERENCE TO RELATED APPLICATIONS

This application claims priority of the Chinese Patent Application No. 201910086054.7, filed on Jan. 29, 2019, the disclosure of which is incorporated by reference herein in its entirety.

TECHNICAL FIELD

The present disclosure relates to the field of wearable device technologies, in particular, to a wearable device, a signal processing method and a signal processing device.

BACKGROUND

As technology enables the human brain to communicate directly with a controlled device, the brain-computer interface (BCI) enables a human to send instructions to an external apparatus outside the human body. A wearable device in the related art may control an electroencephalogram signal and an electrooculogram signal by additionally being provided with a BCI and an electrooculogram signal collecting device, to improve the convenience of human-computer interaction.

SUMMARY

Some embodiments of the present disclosure provide a wearable device including a processor and a signal collector electrically connected to the processor, where the signal collector includes at least one electroencephalogram sensor configured to collect an electroencephalogram signal and at least one electrooculogram sensor configured to collect an electrooculogram signal; and the processor is configured to generate a control signal based on the electroencephalogram signal and the electrooculogram signal, where the electroencephalogram sensor and the electrooculogram sensor are different sensors.

In some embodiments of the present disclosure, the electroencephalogram signal is collected from a steady-state visual evoked potential (SSVEP) channel.

In some embodiments of the present disclosure, the electroencephalogram sensor includes one or more of an O1 sensor, an O2 sensor, an Oz sensor and a Pz sensor.

In some embodiments of the present disclosure, the electroencephalogram sensor includes an O1 sensor, an O2 sensor, an Oz sensor, and a Pz sensor.

In some embodiments of the present disclosure, the wearable device further includes a stimulation generator configured to provide a stimulation signal of which a refresh frequency is not lower than 4 Hz.

In some embodiments of the present disclosure, the stimulation generator includes a display panel or a light-emitting element.

In some embodiments of the present disclosure, the signal collector further includes at least one reference sensor configured to collect a reference signal.

In some embodiments of the present disclosure, the electrooculogram sensor includes at least two horizontal sensors, each of which is configured to collect a signal of a horizontal movement of an eyeball, and at least two vertical sensors, each of which is configured to collect signal of a vertical movement of an eyeball.

In some embodiments of the present disclosure, the signal collector further includes a signal amplifier, a digital to analog converter and a filter which are connected to the electroencephalogram sensor and the electrooculogram sensor.

Some embodiments of the present disclosure further provide a signal processing method applied to any one of the wearable device above, including:

collecting, by the electroencephalogram sensor, the electroencephalogram signal, and collecting, by the electrooculogram sensor, the electrooculogram signal; and processing, by the processor, the electroencephalogram signal and the electrooculogram signal to obtain an electroencephalogram control signal and an electrooculogram control signal, respectively.

In some embodiments of the present disclosure, the signal processing method further including:

before collecting, by the electroencephalogram sensor, the electroencephalogram signal, and collecting, by the electrooculogram sensor, the electrooculogram signal, collecting a first electroencephalogram signal while a preset operation corresponding to the electroencephalogram signal being executed and a first electrooculogram signal while a preset operation corresponding to the electrooculogram signal being executed, and fitting the first electroencephalogram signal to a template signal of the electroencephalogram signal and the first electrooculogram signal to a template signal of the electrooculogram signal; and extracting an electroencephalogram eigenvector for signal classification from the template signal of the electroencephalogram signal and an electrooculogram eigenvector for signal classification from the template signal of the electrooculogram signal.

In some embodiments of the present disclosure, wherein the processing, by the processor, the electroencephalogram signal and the electrooculogram signal to obtain an electroencephalogram control signal and an electrooculogram control signal, respectively, includes:

classifying the electroencephalogram signal to obtain the electroencephalogram control signal based on the electroencephalogram eigenvector; and;

classifying the electrooculogram signal to obtain the electrooculogram control signal based on the electrooculogram eigenvector.

In some embodiments of the present disclosure, the extracting an electroencephalogram eigenvector for signal classification from the template signal of the electroencephalogram signal and an electrooculogram eigenvector for signal classification from the template signal of the electrooculogram signal includes:

converting the template signal of the electroencephalogram signal into a frequency-domain electroencephalogram signal through Fourier transform and the template signal of the electrooculogram signal into a frequency-domain electrooculogram signal through the Fourier transform; and extracting an amplitude of fundamental energy of the frequency-domain electroencephalogram signal as the electroencephalogram eigenvector and an amplitude of fundamental energy of the frequency-domain electrooculogram signal as the electrooculogram eigenvector.

In some embodiments of the present disclosure, the fitting the first electroencephalogram signal to a template signal of the electroencephalogram signal and the first electrooculogram signal to a template signal of the electrooculogram signal includes:

fitting the first electroencephalogram signal to the template signal of the electroencephalogram signal and the first electrooculogram signal to the template signal of the electrooculogram signal through canonical correlation analysis (CCA), wherein the template signal of the electroencephalogram signal and the template signal of the electrooculogram signal each consist of a sine wave signal and a cosine wave signal.

Some embodiments of the present disclosure provide a signal processing device arranged in any one of the wearable device as above, including:

the signal collector, configured to collect the electroencephalogram signal through the electroencephalogram sensor and collect the electrooculogram signal through the electrooculogram sensor; and a signal processor, configured to process the electroencephalogram signal and the electrooculogram signal by the processor to obtain an electroencephalogram control signal and an electrooculogram control signal, respectively.

In some embodiments of the present disclosure, the signal processor includes:

a fitting sub-circuit, configured, before the signal collector collecting the electroencephalogram signal and the electrooculogram signal, to collect a first electroencephalogram signal while a preset operation corresponding to the electroencephalogram signal being executed and a first the electrooculogram signal while a preset operation corresponding to the electrooculogram signal being executed, and fit the first electroencephalogram signal to a template signal of the electroencephalogram signal and the first electrooculogram signal to a template signal of the electrooculogram signal; and an extraction sub-circuit, configured to extract an electroencephalogram eigenvector for signal classification from the template signal of the electroencephalogram signal and an electrooculogram eigenvector for signal classification from the template signal of the electrooculogram signal.

In some embodiments of the present disclosure, the signal processor includes: a classification sub-circuit, configured to classify the electroencephalogram signal to obtain the electroencephalogram control signal based on the electroencephalogram eigenvector and the electrooculogram signal to obtain the electrooculogram control signal based on the electrooculogram eigenvector.

In some embodiments of the present disclosure, the extraction sub-circuit includes:

a converter, configured to convert the template signal of the electroencephalogram signal into a frequency-domain electroencephalogram signal through Fourier transform and the template signal of the electrooculogram signal into a frequency-domain electrooculogram signal through the Fourier transform; and an extractor, configured to extract an amplitude of fundamental energy of the frequency-domain electroencephalogram signal as the electroencephalogram eigenvector and an amplitude of fundamental energy of the frequency-domain electrooculogram signal as the electrooculogram eigenvector.

Some embodiments of the present disclosure provide a wearable device including a processor, a memory and a computer program stored on the memory and executable by the processor, where the computer program causes the processor to execute steps of any of the signal processing method above.

Some embodiments of the present disclosure provide a non-transitory computer-readable storage medium storing computer programs causing the processor to execute steps of any of the signal processing method above.

BRIEF DESCRIPTION OF THE DRAWINGS

In order to illustrate the technical solutions of the embodiments of the present disclosure, the drawings desired for the present disclosure will be described hereinafter briefly. Obviously, the following drawings merely relate to some embodiments of the present disclosure, and based on these drawings, a person skilled in the art may obtain the other drawings without any creative effort.

DETAILED DESCRIPTION

The present disclosure will be described hereinafter in conjunction with the drawings. Obviously, the following relates to some embodiments of the present disclosure instead of all embodiments covered by the claims. Based on these embodiments, other embodiments may be obtained by a person skilled in the art without any creative effort and are also covered by the claims.

In the related art, a wearable device integrated with the BCI and the electrooculogram signal collecting device separates an electrooculogram signal and an electroencephalogram signal from collected signals, with a slow signal response speed and a low response accuracy.

Some embodiments of the present disclosure provide a wearable device.

Figure 1:
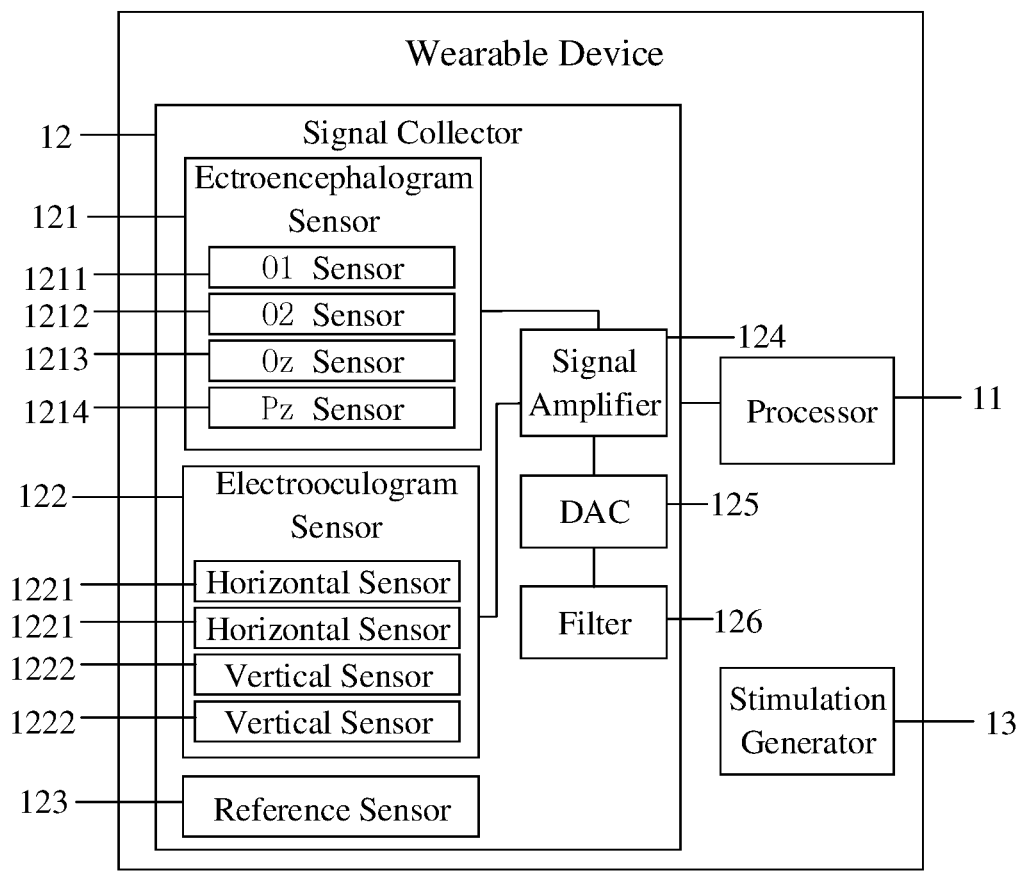
FIG. 1 is a schematic diagram of a wearable device according to some embodiments of the present disclosure.

In some embodiments, as shown in FIG. 1, the wearable device includes a processor 11 and a signal collector 12 electrically connected to the processor 11.

In some embodiments of the present disclosure, the processor 11 is an application processor (AP).

The signal collector 12 includes at least one electroencephalogram sensor 121 configured to collect an electroencephalogram (EEG) signal and at least one electrooculogram sensor 122 configured to collect an electrooculogram (EOG) signal. The processor 11 is configured to generate a control signal, that is, an electroencephalogram control signal and an electrooculogram signal, based on the electroencephalogram signal and the electrooculogram signal collected by the signal collector 12.

The electroencephalogram sensor 121 and the electrooculogram sensor 122 are different sensors.

Some embodiments below illustrate some examples in which an electrode for collecting the electroencephalogram signal is used as the electroencephalogram sensor and an electrode for collecting the electrooculogram signal is used as the electrooculogram sensor.

For example, the electrode for collecting the electroencephalogram signal is an electroencephalogram electrode patch, and when used to collect signals, the electroencephalogram electrode patch is attached to the head of a user to obtain the user's electroencephalogram signal, also named brain waves. When the brain performs some specific activities or suffers some particular stimulations, electrophysiological activities occur in the cerebral cortex or on a surface of the scalp, and at the same time, a brain signal is modulated into a special signal that is easily recognized, where the special signal is referred to as a canonical form of the electroencephalogram signal paradigm.

The electrode for collecting the electrooculogram signal is referred to as an electrooculogram electrode, and when used to collect signals, the electrooculogram electrode is provided near the user's eyes to detect the electrooculogram signal of the user. The electrooculogram signal is a bioelectrical signal produced by a potential difference between cornea and retina of the eye. A waveform of the electrooculogram signal has a direct correspondence with the movement state of an eyeball, and thus such movement state may be detected by detecting the electrooculogram signal.

In the above-mentioned embodiments of the present disclosure, the electroencephalogram sensor for collecting the electroencephalogram signal is different from the electrooculogram sensor for collecting the electrooculogram signal. In this way, when the electroencephalogram sensor and the electrooculogram sensor are used to detect signals, the signal collected by the electroencephalogram sensor and the signal collected by the electrooculogram sensor may be directly used as the electroencephalogram signal and the electrooculogram signal respectively, and the collected electroencephalogram signal and electrooculogram signal may be processed to obtain the electroencephalogram control signal and the electrooculogram control signal, respectively.

Compared to cases where one sensor is used as not only the electroencephalogram sensor but also the electrooculogram sensor, or at least one sensor is commonly used by the electroencephalogram sensor and the electrooculogram sensor, signals collected are not separated or extracted in the technical solution of the embodiments of the present disclosure, thus the response speed is increased. Additionally, in the solution of the embodiments of the present disclosure, no errors produced by signal separation or extraction are generated, and the signal accuracy is improved.

In some embodiments of the present disclosure, the wearable device is a remote controlled device (e.g., a helmet, glasses, bandages, or the like), an Augmented Reality (AR) device, or a Virtual Reality (VR) device.

In some embodiments of the present disclosure, the electroencephalogram signal is collected from a steady-state visual evoked potential (SSVEP) channel.

In some embodiments of the present disclosure, the electroencephalogram sensor 121 includes one or more of an O1 sensor, an O2 sensor, an Oz sensor and a Pz sensor.

For example, as shown in FIG. 1, the electroencephalogram sensor 121 includes one or more of an O1 sensor 1211, an O2 sensor 1212, an Oz sensor 1213 and a Pz sensor 1214.

There is a plurality of canonical forms of the electroencephalogram signal. Different electroencephalogram signal paradigms may be selected to obtain the electroencephalogram signal.

In some embodiments of the present disclosure, the electroencephalogram signal collected from the SSVEP channel is employed.

A signal in the SSVEP channel is a periodic signal that tends to be stable over time and has a fixed spectral feature that peaks at a point of applying a stimulation frequency. In addition, signal collected from SSVEP has a higher signal-to-noise ratio (SNR) and a faster information transfer rate (ITR) than some canonical forms of the electroencephalogram signals, such as collected from event-related potential (ERP) and event related synchronization/desynchronization (ERS/ERD). Therefore, the generation of a control signal by collecting the electroencephalogram signal of the SSVEP channel contributes to the improvements of the signal response speed and information transfer rate, and also of the control accuracy of the signal. If too many collecting sensors are provided, e.g., 40 conductive electrode caps, the portability and wearability of the wearable device would be seriously affected.

Figure 2A:
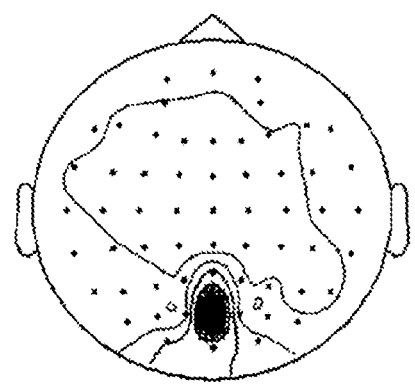
FIG. 2A illustrates a brain electrical activity mapping (BEAM) responding to the SSVEP according to some embodiments of the present disclosure.
Figure 2B:
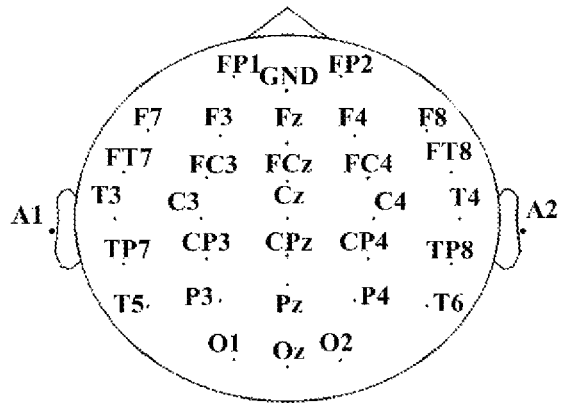
FIG. 2B illustrates a distribution diagram of collection channels of the ten twenty electrode system as defined in the international standards.

FIG. 2A illustrates a brain electrical activity mapping (BEAM) responding to the SSVEP. FIG. 2B illustrates a distribution diagram of collection channels of the ten twenty electrode system as defined in the international standards, with the collecting channels, such as A1, F4, P3, and CPz, marked in black dots in FIG. 2.

In the case where other conditions are the same, the information contained in the collected electroencephalogram signal is independent of the number of collected signal channels, which only affects the signal accuracy. That is, the electroencephalogram signals acquired by the signal collected from one channel and the signal collected from a plurality of channels are the same, but the electroencephalogram signal acquired through the signal collected from a plurality of channels is more accurate than that acquired through the signal collected from one channel.

The greater the number of collected channels, the greater the number of sensors. Since the wearable device is worn on the head of the user, the greater the number of sensors, the greater the load on the head of the user, the lower the comfort level, so the number of collected channels of the signal and their positions should be reasonably controlled.

In some embodiments, the electroencephalogram sensor includes one or more of an O1 sensor, an O2 sensor, an Oz sensor and a Pz sensor, where the O1 sensor, O2 sensor, Oz sensor, and Pz sensor correspond to the O1 channel, O2 channel, Oz channel and Pz channel, respectively, and are configured to collect the electroencephalogram signals of the corresponding channels.

For example, each of the O1 sensor, the O2 sensor, the Oz sensor, and the Pz sensor is a sensing electrode.

For normal users, amplitude of brain waves of the four channels, O1, O2, Oz and Pz, are greater than those of brain waves of other channels (e.g., F3, F4, F8, F7, T3, T4, T5 and T6), so one or more of the four channels may be selected to collect the electroencephalogram signal, which may not only guarantee the amplitude of the collected electroencephalogram signal, but also reduce the number of electroencephalogram sensors.

In some embodiments, the electroencephalogram sensor 121 includes an O1 sensor 1211, an O2 sensor 1212, an Oz sensor 1213 and a Pz sensor 1214.

The electroencephalogram signals collected from the O1 channel, O2 channel, Oz channel and Pz channel with relatively high signal amplitude are collected by providing the O1 sensor, O2 sensor, Oz sensor, and Pz sensor, respectively, which may on the one hand, guarantee the accuracy of the collected electroencephalogram signal, one the other hand, reduce the number of sensors.

In some embodiments of the present disclosure, the signal collector 12 further includes at least one reference sensor 123 configured to collect the reference signal.

In order to improve an analysis accuracy of the electroencephalogram signal and the electrooculogram signal, a reference signal is provided as a reference.

In some embodiments of the present disclosure, the reference signal has a preset value.

The electroencephalogram signal and the electrooculogram signal are analyzed on basis of the preset value of the reference signal.

In some embodiments, a reference sensor is provided.

The reference signal is collected by the reference sensor, thereby analyzing the electroencephalogram signal and/or the electrooculogram signal based on the reference signal.

In some embodiments of the present disclosure, the reference sensor 123 is arranged on a forehead of a user, to collect a signal of a GND channel as a reference signal.

A potential difference between a sensor (e.g., O1 sensor 1211, an O2 sensor 1212, an Oz sensor 1213 or a Pz sensor 1214) and the reference sensor is collected as a value of a signal collected by the sensor, which contributes to the improvement of the accuracy of signal analysis.

In some embodiments of the present disclosure, the electrooculogram sensor 122 includes at least two horizontal sensors 1221, each of which is configured to collect a signal of a horizontal movement of an eyeball, and at least two vertical sensors 1222, each of which is configured to collect a signal of a vertical movement of the eyeball.

For example, the electrooculogram sensor includes two horizontal sensors and two vertical sensors. The two horizontal sensors include HEOL arranged at a position with a distance about 2.5 cm from a left eye of a user, and HEOR arranged at a position with a distance about 2.5 cm from a right eye of the user. The two vertical sensors include VEOU arranged at a position with a distance about 2 cm above the right eyebrow of the user, and VEOL arranged at a position with a distance about 2 cm below the right eye of the user.

The position of the electrooculogram sensor may be adjusted adaptively as needed.

The cerebral cortex of human may generate the electroencephalogram signal in the SSVEP channel only when the retina is stimulated by a target with a specific flicker frequency.

In order to generate the electroencephalogram signal in the SSVEP channel in a user's brain, a stimulation signal may be provided, and the stimulation signal has a certain flicker frequency. The feature of the electroencephalogram signal generated is determined only by the flicker frequency of the stimulation signal and has nothing to do with other parameters of the stimulation signal.

In some embodiments, other apparatuses, such as a television, a display device, and so on, are used to stimulate the cerebral cortex of the user.

In some other embodiments, the wearable device further includes a stimulation generator 13 which is configured to provide a stimulation signal of which a refresh frequency is not lower than 4 Hz.

The stimulation signal has a refresh frequency of not lower than 4 Hz, to applying the stimulation to the brain of the user.

In some embodiments, the stimulation generator 13 includes a display panel or a light-emitting element.

For example, an image which is refreshed regularly is displayed by at least a part of a display panel to provide the stimulation signal, or a light-emitting element, such as a light-emitting diode, is deployed to turn on at a certain frequency, which provides the stimulation signal.

In some embodiments, the signal collector 12 further includes a signal amplifier 124, a digital to analog converter (DAC) 125 and a filter 126 which are connected to the electroencephalogram sensor and the electrooculogram sensor.

The signal amplifier 124 is configured to amplify the collected signal, to improve the recognizability of the electroencephalogram signal and the electrooculogram signal. The digital to analog converter 125 is configured to convert a collected digital signal into an analog signal processable by the processor. The filter 126 is configured to remove noise from signals.

Some embodiments of the present disclosure further provide a signal processing method, applied to any one of the wearable device as mentioned above.

Figure 3:
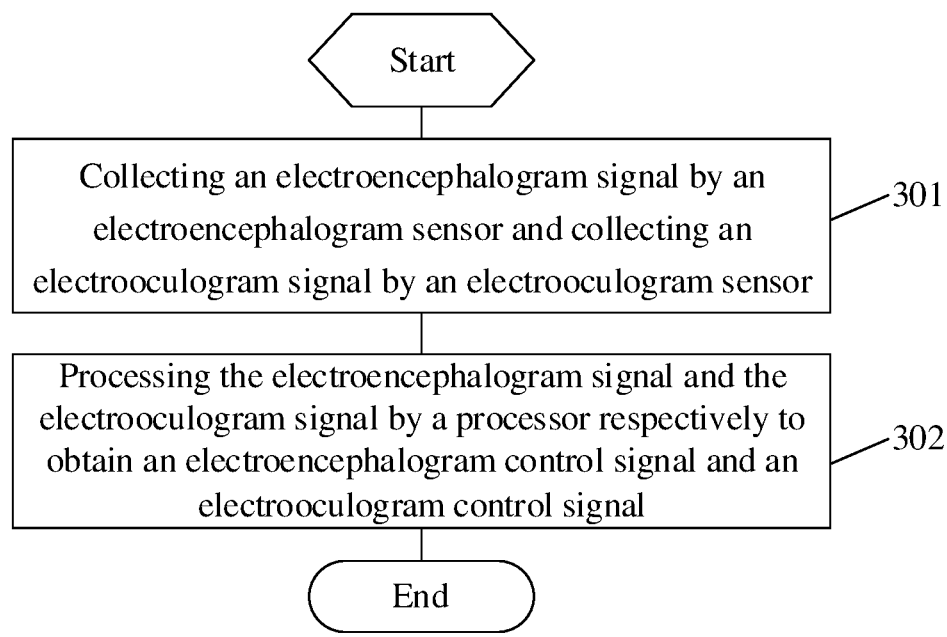
FIG. 3 is a flow chart of a signal processing method according to some embodiments of the present disclosure.

In some embodiments, as shown in FIG. 3, the signal processing method includes steps 301 and 302.

In the step 301, an electroencephalogram signal is collected by the electroencephalogram sensor, and an electrooculogram signal is collected by the electrooculogram sensor.

Since the electroencephalogram sensor is sensor different from the electrooculogram sensor, the signal collected by the electroencephalogram sensor is the electroencephalogram signal to be directly processed, and the signal collected by the electrooculogram sensor is the electrooculogram signal to be directly processed.

In the step 302, the electroencephalogram signal and the electrooculogram signal are processed by the processor to obtain an electroencephalogram control signal and an electrooculogram control signal, respectively.

The electroencephalogram signal is collected while a user performs an electroencephalogram control operation, and the electrooculogram signal is collected while a user performs an electrooculogram control operation.

Figure 4:
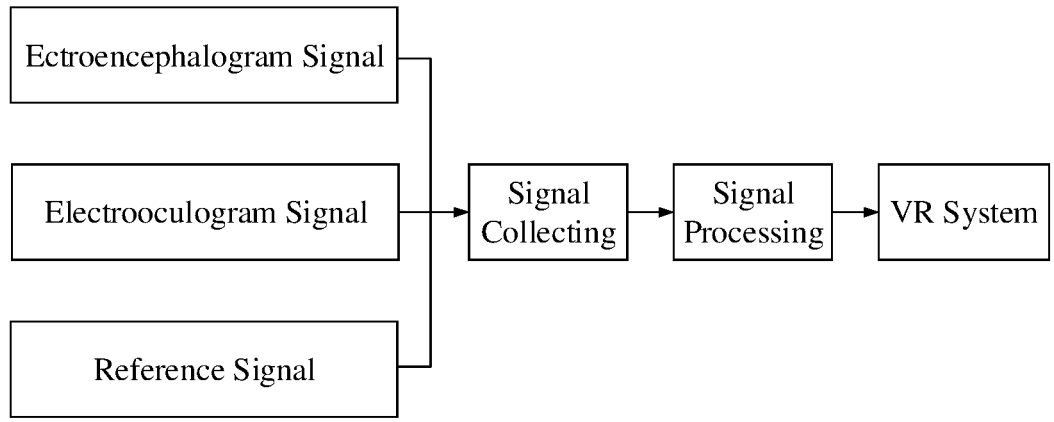
FIG. 4 is a working diagram of a VR system according to some embodiments of the present disclosure.
Figure 5:
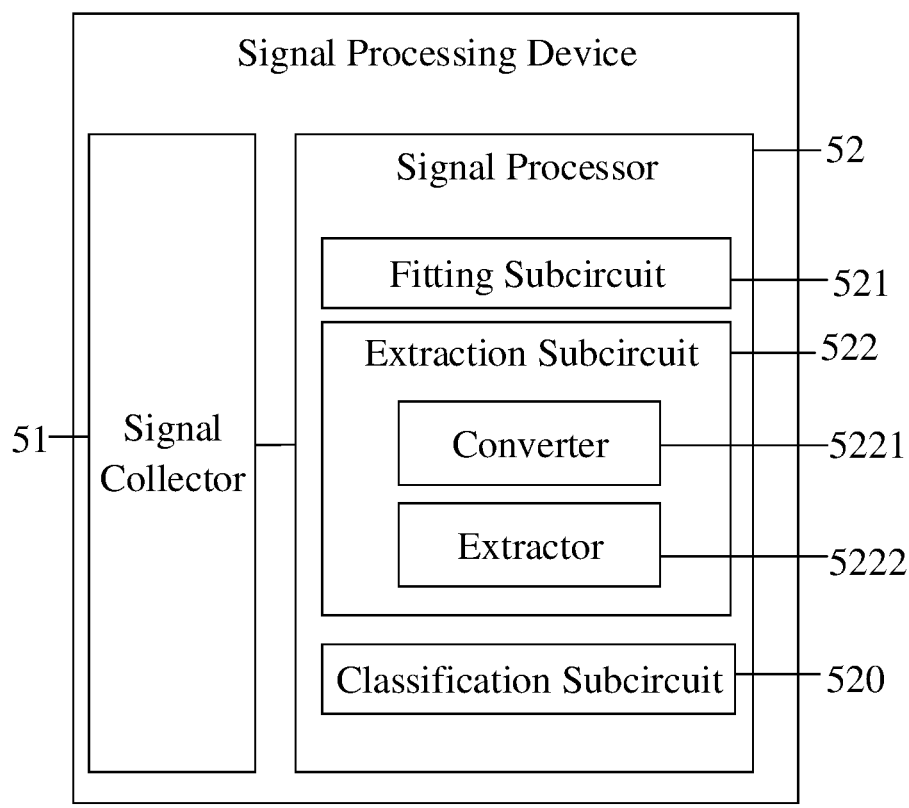
FIG. 5 is a schematic diagram of a signal processing device according to some embodiments of the present disclosure.
Figure 6:
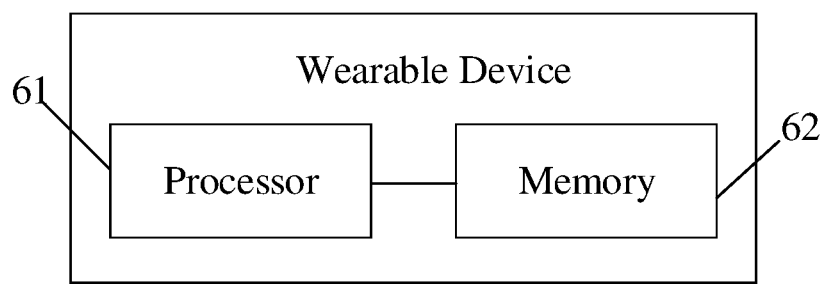
FIG. 6 is a schematic diagram of the wearable device according to some other embodiments of the present disclosure.

In some embodiments of the present disclosure, as shown in FIG. 4, the electroencephalogram signal is collected by the electroencephalogram sensor, the electrooculogram signal is collected by the electrooculogram sensor, and the reference signal is collected by the reference sensor. The collected signals is subjected to data processing, and data obtained after the data processing are transmitted to the VR system and then is process using the VR control algorithm. Thus, a control signal of the electroencephalogram signal and a control signal of the electrooculogram signal are generated, which are used to assist human-machine interaction and operations to the VR device.

Since the electroencephalogram sensor is a sensor different from the electrooculogram sensor, signals are not subjected to separation or extraction in the technical solution of the embodiments of the present disclosure, thus the response speed is increased. Additionally, in the solution of the embodiments, errors generated by signal separation and extraction are not produced, and the signal accuracy is improved.

In some embodiments of the present disclosure, an electroencephalogram control signal is determined based on a template signal of the electroencephalogram control signal, which is preset, and an electrooculogram control signal is determined based on a template signal of the electrooculogram signal, which is preset.

Since the electroencephalogram signal and the electrooculogram signal of one user may differ from that of others, the electroencephalogram signal and the electrooculogram signal of a same user in one state may also differ from that of the same user in other states. In some embodiments, the electroencephalogram signal and the electrooculogram signal are tested to determine the template signal.

For example, the template signal of the electroencephalogram control signal and the template signal of the electrooculogram signal are determined before a user performs the electroencephalogram control operation wearable device and the electrooculogram control operation, respectively.

In some embodiments, before the step 301, the signal processing method further includes steps 3001 and 3002.

In the step 3001, a first electroencephalogram signal is collected while a preset operation corresponding to the electroencephalogram signal being executed by a user, and a first electrooculogram signal is collected while a preset operation corresponding to the electrooculogram signal being executed by a user; and the first electroencephalogram signal is fit to a template signal of the electroencephalogram signal, and the first electrooculogram signal is fit to a template signal of the electrooculogram signal.

In the step 3002, an electroencephalogram eigenvector for signal classification is extracted from the template signal of the electroencephalogram signal, and an electrooculogram eigenvector for signal classification is extracted from the template signal of the electrooculogram signal.

In some embodiments, the step 302 includes, classifying the electroencephalogram signal to obtain the electroencephalogram control signal based on the electroencephalogram eigenvector, and classifying the electrooculogram signal to obtain the electrooculogram control signal based on the electrooculogram eigenvector.

For example, the user performs preset operations, such as the preset operation corresponding to the electroencephalogram signal and the preset operation corresponding to the electrooculogram signal, as required, to determine the template signal of the electroencephalogram signal and the template signal of the electrooculogram signal.

For another example, the preset operation corresponding to the electroencephalogram signal is to observe at least two regions with different flicker frequencies on the display panel by the user.

An electroencephalogram signal generated by observing a first region of a display panel by a user is different from that generated by observing a second region different from the first region by the user. When the user performs a preset operation, a electroencephalogram signal generated by observing a region of a display panel by a user is collected as the template signal of the electroencephalogram signal corresponding to the region.

Similarly, the electrooculogram signal is generated by the movement of an eyeball, so the preset operation is set corresponding to movements of the eyeball of the user in different directions, for example, sequentially upwards, downwards, leftwards and rightwards. When the user performs a preset operation, the electrooculogram signal is collected and used as a template signal of the electrooculogram signal.

In some embodiments, fitting processes adopts canonical correlation analysis (CCA).

For example, the first electroencephalogram signal and the first electrooculogram signal are processed by the canonical correlation analysis to be fit to the template signal of the electroencephalogram signal and template signal of the electrooculogram signal respectively, each of which consists of a sine wave signal and a cosine wave signal.

In some embodiments, a template signal (i.e., template signal of the electroencephalogram signal and/or template signal of the electrooculogram signal) is defined as a variable group Y. For the electroencephalogram signal, its expression formula (1) is as follows:

$$Y = \begin{bmatrix} \sin\left(\frac{2\pi f_1}{f_s}t\right); \cos\left(\frac{2\pi f_1}{f_s}t\right) \\ \sin\left(\frac{2\pi f_2}{f_s}t\right); \cos\left(\frac{2\pi f_2}{f_s}t\right) \\ \vdots \\ \sin\left(\frac{2\pi f_2}{f_s}t\right); \cos\left(\frac{2\pi f_s}{f_s}t\right) \end{bmatrix}, \quad (1)$$

where $f_i$ represents a stimulation frequency of the ith stimulation signal, $f_s$ represents a stimulation frequency of a standard stimulation signal, and t represents a sequence number ranging from 1 to L.

In a process of extracting the electroencephalogram eigenvector for signal classification from the template signal of the electroencephalogram signal, when the eyeball moves in a same direction or an approximate direction, e.g., moves rightwards, the electrooculogram signals generated in such direction are substantially the same, and the eigenvector of this electrooculogram signal is extracted and acts as the eigenvector when the eyeball of the user moves rightwards.

Similarly, eigenvectors of the electroencephalogram signal generated by the user subjected to different stimulation signals may also be extracted.

In some embodiments, the step 3002 includes:

converting the template signal of the electroencephalogram signal into a frequency-domain electroencephalogram signal through Fourier transform and the template signal of the electrooculogram signal into a frequency-domain electrooculogram signal through the Fourier transform; and extracting an amplitude of fundamental energy of the frequency-domain electroencephalogram signal as the electroencephalogram eigenvector and an amplitude of fundamental energy of the frequency-domain electrooculogram signal as the electrooculogram eigenvector.

The Fourier transform is a commonly used signal analysis method. The template signal subjected to Fourier transform is converted into the frequency-domain signal, such as the frequency-domain electroencephalogram signal and the frequency-domain electrooculogram signal. An amplitude of fundamental energy of the frequency-domain signal is taken as an eigenvector such as the electroencephalogram eigenvector and electrooculogram signal, and the eigenvector corresponds to a preset operation performed by the user.

When the user performs a control operation, the electroencephalogram signal and the electrooculogram signal are collected by the electroencephalogram sensor and the electrooculogram sensor respectively. In the following embodiments, an example in which four electroencephalogram sensors and four electrooculogram sensors are illustrated is described, and thus four channels of the electroencephalogram signal and four channels of the electrooculogram signal are collected.

The four channels of the electroencephalogram signal is defined as a variable group X expressed by the formula (2):

$$X = \begin{bmatrix} channel_1 \\ channel_2 \\ channel_3 \\ channel_4 \end{bmatrix}, \quad (2)$$

where one channel represents the electroencephalogram signal in one channel.

Similarly, the four channels of the electrooculogram signal may also be defined as the variable group X, where one channel represents an electrooculogram signal in one channel.

By comparing and classifying the variable group X and the eigenvector obtained by the variable group Y, a mapping relationship between the signal of the variable group X and the template signal is established.

For example, in a case where the variable group X represents the electrooculogram signal, and a first signal in X is classified in the same category with the eigenvector of the template signal generated by the eyeball moving rightwards in the variable group Y of the electrooculogram signal, the first signal in the variable group X is regarded as being generated while the eyeball of the user move rightwards, i.e., the user sends a control signal corresponding to the rightward movement of the eyeball.

In some embodiments of the present disclosure, an artificial intelligence classification algorithm is used to classify signals with frequency features.

For example, the artificial intelligence classification algorithm for classifying the electroencephalogram signals and the electrooculogram signals includes, but not limited to, the support vector machine (SVM), and so on.

For example, the electroencephalogram signals and the electrooculogram signals each are classified by a SVM classification function which is constructed based on a kernel function.

The SVM classification function which is based on a kernel function is constructed as the following formula (3):

$$f(x) = \text{sgn}\left(\sum_{i=1}^{N} a_i y_i K(x_i, x) + b\right) \quad (3)$$

where $K(x_i, x)$ is the kernel function selected, for example the kernel function in the related art, such as a polynomial kernel, radial basis function kernel, Sigmoid kernel or Laplacian kernel, $a_i$ and $y_i$ each are Lagrangian multipliers, and b is an intercept of the regression analysis.

Sgn is a sign function with only three function values of 1, 0, −1. The function value of 1 represents that a value in brackets is greater than 0, the function value of 0 represents that the value in brackets is equal to 0, and the function value of −1 represents that the value in brackets is less than 0.

Taking the electroencephalogram signal as an example, in a case where the function value is 1, the eigenvector of the electroencephalogram signal currently collected and the eigenvector of the electroencephalogram signal extracted from the template signal of the electroencephalogram signal may be classified into the same category. In a case where the function value is −1 or 0, the eigenvector of the electroencephalogram signal currently collected and the eigenvector of the electroencephalogram signal extracted from the template signal of the electroencephalogram signal may not be classified into the same category.

Taking the electrooculogram signal as an example, in a case where a returned value for the classification result of a signal x1 in the vector group X of the electrooculogram signal and a eigenvector y2 in the vector group Y of the electrooculogram signal is 1, and a returned value for the classification result of the signal x1 in the vector group X of the electrooculogram signal and other eigenvectors in the vector group Y of the electrooculogram signal is 0, it is indicated that the signal x1 in the vector group X and the eigenvector y2 in the vector group Y may be classified into the same category. This means that the user sends a control signal corresponding to a template signal corresponding to y2. For example, if the eigenvector y2 in the vector group Y indicates that the eyeball moves rightwards, it is considered that the user sends the control signal corresponding to a rightward movement of the eyeball.

By classifying the electroencephalogram signal and the electrooculogram signal collected when the user performs the control operation, the electroencephalogram control signal and the electrooculogram control signal sent by the user may be determined, thereby performing corresponding control operations.

In the following, a signal processing method applied to game control will be illustrated.

Since the electrooculogram signal is generated in accordance with the moving direction of the eyeball, in some embodiments of the present disclosure, the direction in the game is controlled through the electrooculogram signal, for example, the moving direction of the character in the game, or the like.

The following description is made by taking the electrooculogram signal corresponding to upward, downward, rightward and leftward movements of eyeball respectively corresponding to upward, downward, rightward and leftward operations in the game as an example.

In some other embodiments of the present disclosure, the electrooculogram signals corresponding to upward and downward movements of eyes correspond to the forward and backward operations in the game respectively.

In some other embodiments of the present disclosure, the electrooculogram signals corresponding to a plurality of movements of eyeball are divided into three categories, i.e., forward movement, leftward movement and rightward movement.

By setting such corresponding correspondence, the control over the direction of the game manipulation may be realized through the electrooculogram signal.

The user performs a preset operation corresponding to the electrooculogram signal, which includes looking upwards, downwards, leftwards and rightwards at designated moment or in designed time periods. The corresponding electrooculogram signal is collected according to the preset operation, and the eigenvectors of the electrooculogram signal are extracted as the eigenvectors of the template signal of looking upwards, downwards, leftwards and rightwards.

When a user performs the control operation, for example, when the user performs the game control operation, in the case where the eigenvector of the electrooculogram signal collected and the eigenvector of the template signal corresponding to a looking upwards operation may be classified into the same category, it is considered that the user sends a control signal of upward operation to control the game.

The classification of the electrooculogram signal is determined by the number of excitation targets, and different excitation targets have different flicker frequencies. For example, the stimulation signal is provided by continuous flickering in a specific region on the display panel, and one specific region may provide one excitation target. When there are a plurality of specific regions on the display panel, a plurality of excitation targets may be provided correspondingly.

For example, each excitation target corresponds to one corresponding item. When one item is applied to a different operations, it corresponds to different contents.

In a condition where the signal processing method is applied to a shooting game, different items correspond to different weapons, which is taken as an example to make the following descriptions.

The display panel has a plurality of regions corresponding to weapons. Since each of the regions corresponds to one weapon and regions are different in the flicker frequency, and the electroencephalogram signal collected from the SSVEP channel has nothing to do with the displayed contents, the region corresponding to each weapon may display various contents. For example, in order to increase the recognizability, the name or icon of the weapon is selected to be displayed.

For example, the user firstly performs a preset operation, which is to gaze at different regions within designated periods. In this way, the electroencephalogram signal when the user gazes at different regions may be collected, and the corresponding eigenvector is extracted.

When the user performs the control operation, for example, a game control operation, in the case where the eigenvector of the collected electroencephalogram signal and the eigenvector of the template signal of the region A may be classified into the same category, it is indicated that the user is gazing at the region A and sends the control signal of switching the weapon to the weapon corresponding to the region A.

In some other embodiments, for example when the signal processing method is applied to a fighting game, different items correspond to different moves (i.e., fighting postures). When the signal processing method is applied to a card game, different items correspond to different cards.

Some embodiments of the present disclosure further provide a signal processing device arranged in any one of the wearable device above. The signal processing device includes a signal collector 51 and a signal processor 52.

The signal collector 51 is configured to collect an electroencephalogram signal through the electroencephalogram sensor, and collect an electrooculogram signal through the electrooculogram sensor.

The signal processor 52 is configured to process the electroencephalogram signal and the electrooculogram signal by the processor respectively to obtain an electroencephalogram control signal and an electrooculogram control signal.

In some embodiment of the present disclosure, the signal processor 52 includes a fitting sub-circuit 521 and an extraction sub-circuit 522.

The fitting sub-circuit 521 is configured, before the signal collector collecting the electroencephalogram signal and the electrooculogram signal, to collect a first electroencephalogram signal while a preset operation corresponding to the electroencephalogram signal being executed and a first the electrooculogram signal while a preset operation corresponding to the electrooculogram signal being executed, and fit the first electroencephalogram signal to a template signal of the electroencephalogram signal and the first electrooculogram signal to a template signal of the electrooculogram signal.

The extraction sub-circuit 522 is configured to extract an electroencephalogram eigenvector for signal classification from the template signal of the electroencephalogram signal and an electrooculogram eigenvector for signal classification from the template signal of the electrooculogram signal.

In some embodiments of the present disclosure, the signal processor 52 further includes the classification sub-circuit 523 configured to classify the electroencephalogram signal to obtain the electroencephalogram control signal based on the electroencephalogram eigenvector and the electrooculogram signal to obtain the electrooculogram control signal based on the electrooculogram eigenvector.

In some embodiment of the present disclosure, the extraction sub-circuit 522 includes a converter 5221 and an extractor 5222.

The converter 5221 is configured to convert the template signal of the electroencephalogram signal into a frequency-domain electroencephalogram signal through Fourier transform and the template signal of the electrooculogram signal into a frequency-domain electrooculogram signal through the Fourier transform.

The extractor 5222 is configured to extract an amplitude of fundamental energy of the frequency-domain electroencephalogram signal as the electroencephalogram eigenvector and an amplitude of fundamental energy of the frequency-domain electrooculogram signal as the electrooculogram eigenvector.

The signal processing device according to embodiments above has at least all the technical effects of the embodiments of the signal processing method, which are not repeated herein, since it may implement all the technical solutions of the signal processing method according to the embodiments above.

Some embodiments of the present disclosure further provide a wearable device, including a processor 61, a memory 62 and a computer program stored on the memory and executable by the processor, where the computer program causes the processor to execute steps of the signal processing method above.

Some embodiments of the present disclosure further provide a computer-readable storage medium storing computer programs causing the processor to execute steps of the signal processing method.

In some embodiments of the present disclosure, the computer readable storage medium includes a non-transitory computer readable storage medium and a transitory computer readable storage medium.

For example, the computer-readable storage medium includes a phase change memory (PRAM), a random access memory (RAM), a static random access memory (SRAM), a dynamic random access memory (DRAM), a read only memory (ROM), an electrically erasable programmable read only memory (EEPROM), a compact disc read only memory (CD-ROM), and a digital versatile disc (DVD).

Through the description of the embodiments above, those skilled in the art clearly appreciate that the present disclosure may be implemented by means of software and hardware, and, of course, may also be implemented only by hardware. All or part of the technical solutions of the present disclosure may be embodied in the form of a software product, which may be stored in a storage medium such as a ROM/RAM, a magnetic disk, an optical disk, etc., and includes a plurality of instructions causing a computer device (e.g., a personal computer, a server, or a network device, or the like) to execute the method according to all or part of the embodiments of the present disclosure.

The descriptions above only illustrate some embodiments of the present disclosure, but shall not be used to limit the scope of the present disclosure. Any modifications or alternations to these embodiments made by persons skilled in the art within the technical scope of the present disclosure shall also fall within the scope of the present disclosure as defined by the claims.

What is claimed is:
1. A wearable device, wherein the wearable device is an augmented reality (AR) device or a virtual reality (VR)

device comprising a processor, a signal collector electrically connected to the processor, and a stimulation generator configured to provide a stimulation signal;
- wherein the stimulation generator comprises a display panel capable of displaying at different regions with different flicker frequencies to trigger a generation of different electroencephalogram signals;
- wherein the signal collector comprises exactly four electroencephalogram sensors configured to collect electroencephalogram signals and at least one electrooculogram sensor configured to collect electrooculogram signals, the four electroencephalogram sensors consisting of an O1 sensor, an O2 sensor, an Oz sensor, and a Pz sensor;
- wherein the processor is configured to:
  - fit, through canonical correlation analysis (CCA), first electroencephalogram signals to a template signal for electroencephalogram signals, wherein the first electroencephalogram signals are collected by the signal collector while a preset operation corresponding to electroencephalogram signals is being executed, the preset operation corresponding to electroencephalogram signals comprises observing at least two regions with different flicker frequencies on the display panel by a user, such that I stimulation signals are provided, with the template signal for electroencephalogram signals being denoted as a first variable group Y defined as:

$$Y = \begin{bmatrix} \sin\left(\frac{2\pi f_1}{f_s}t\right); \cos\left(\frac{2\pi f_1}{f_s}t\right) \\ \sin\left(\frac{2\pi f_2}{f_s}t\right); \cos\left(\frac{2\pi f_2}{f_s}t\right) \\ \vdots \\ \sin\left(\frac{2\pi f_i}{f_s}t\right); \cos\left(\frac{2\pi f_i}{f_s}t\right) \end{bmatrix},$$

where $f_i$ represents a stimulation frequency of the i-th stimulation signal, $f_s$ represents a stimulation frequency of a standard stimulation signal, and t represents a sequence number ranging from 1 to L, I and i both being positive integers, and I being greater than or equal to i;
  - fit, through the CCA, first electrooculogram signals to a template signal for electrooculogram signals, wherein the first electrooculogram signals are collected by the signal collector while a preset operation corresponding to electrooculogram signals is being executed, and the template signal for electroencephalogram signals and the template signal for electrooculogram signals each consists of a sine wave signal and a cosine wave signal;
  - extract, from the first variable group by using Fourier transform, an electroencephalogram eigenvector for an electroencephalogram signal classification;
  - extract, from the template signal for electrooculogram signals by using Fourier transform, an electrooculogram eigenvector for an electrooculogram signal classification;
  - cause the four electroencephalogram sensors to collect four channels of electroencephalogram signals in real time, the four electroencephalogram channels of signals being denoted as a second variable group X defined as:

$$X = \begin{bmatrix} channel_1 \\ channel_2 \\ channel_3 \\ channel_4 \end{bmatrix};$$

- generate a first control signal based on a first classification result obtained by using the second variable group and the electroencephalogram eigenvector, the first control signal indicating a target region in the at least two regions; and
  - generate a second control signal based on a second electrooculogram signal collected by the signal collector in real time, and the electrooculogram eigenvector;
- wherein the processor is further configured to cause the wearable device to:
  - perform a moving operation for a character in an application according to the second control signal; and
  - perform a control operation for the target region in the application according to the first control signal.

2. The wearable device according to claim 1, wherein the electroencephalogram signals are collected from a steady-state visual evoked potential (SSVEP) channel.

3. The wearable device according to claim 1, wherein when generating the first control signal based on the first classification result obtained by using the second variable group and the electroencephalogram eigenvector, the processor is further configured to:
- input the second variable group and the electroencephalogram eigenvector into a support vector machine (SVM) classification function to obtain the first classification result, wherein the SVM classification function is:

$$f(x) = \text{sgn}\left(\sum_{i=1}^{N} a_i y_i K(x_i, x) + b\right),$$

wherein $K(x_i, x)$ is a kernel function, $a_i$ and $y_i$ are Lagrangian multipliers, and b is an intercept of a regression analysis; and the first classification result is determined based on whether an output value of the SVM classification function is equal to 1.

4. The wearable device according to claim 3, wherein the at least one electrooculogram sensor consists of four electrooculogram sensors, the four electrooculogram sensors are two horizontal sensors, each of which is configured to collect a signal of a horizontal movement of an eyeball, and two vertical sensors, each of which is configured to collect a signal of a vertical movement of the eyeball; the preset operation corresponding to electrooculogram signals comprises moving an eyeball by the user in different moving directions, the second electrooculogram signal is four channels of electrooculogram signals collected by the four electrooculogram sensors, and the four channels of electrooculogram signals are denoted as a third variable group X1 defined as:

$$X1 = \begin{bmatrix} channel_1 \\ channel_2 \\ channel_3 \\ channel_4 \end{bmatrix};$$

wherein when generating the second control signal based on the second electrooculogram signal and the electrooculogram eigenvector, the processor is further configured to:
  generate the second control signal based on a second classification result obtained by using the third variable group and the electrooculogram eigenvector, the second control signal indicates a target moving direction in the different moving directions.

5. The wearable device according to claim 4, wherein when generating the second control signal based on the second classification result obtained by using the third variable group and the electrooculogram eigenvector, the processor is further configured to:
  input the third variable group and the electrooculogram eigenvector into a support vector machine (SVM) classification function to obtain the second classification result, wherein the SVM classification function is:

$$f(x) = \text{sgn}\left(\sum_{i=1}^{N} a_i y_i K(x_i, x) + b\right),$$

wherein $K(x_i, x)$ is a kernel function, $a_i$ and $y_i$ are Lagrangian multipliers, and b is an intercept of a regression analysis; and the second classification result is determined based on whether an output value of the SVM classification function is equal to 1.

6. The wearable device according to claim 1, wherein each of the stimulation signals has a frequency not lower than 4 Hz.

7. The wearable device according to claim 1, wherein the signal collector further comprises at least one reference sensor configured to collect a reference signal.

8. The wearable device according to claim 1, wherein the signal collector further comprises a signal amplifier, a digital to analog converter, and a filter, which are connected to the electroencephalogram sensor and the electrooculogram sensor.

9. A signal processing method, performed by a wearable device, the wearable device being an augmented reality (AR) device or a virtual reality (VR) device comprising a processor a signal collector electrically connected to the processor, and a stimulation generator configured to provide a stimulation signal, the stimulation generator comprising a display panel capable of displaying at different regions with different flicker frequencies to trigger a generation of different electroencephalogram signals, the method comprising:
  collecting, by four electroencephalogram sensors of the signal collector, first electroencephalogram signals while a preset operation corresponding to electroencephalogram signals is being executed, wherein the four electroencephalogram sensors consist of an O1 sensor, an O2 sensor, an Oz sensor, and a Pz sensor, and wherein the preset operation corresponding to electroencephalogram signals comprises observing at least two regions with different flicker frequencies on the display panel by a user, such that I stimulation signals are provided;
  collecting, by at least one electrooculogram sensor of the signal collector, first electrooculogram signals while a preset operation corresponding to electrooculogram signals is being executed;
  fitting, by the processor through canonical correlation analysis (CCA), the first electroencephalogram signals to a template signal for electroencephalogram signals which is denoted as a first variable group Y defined as:

$$Y = \begin{bmatrix} \sin\left(\frac{2\pi f_1}{f_s}t\right); \cos\left(\frac{2\pi f_1}{f_s}t\right) \\ \sin\left(\frac{2\pi f_2}{f_s}t\right); \cos\left(\frac{2\pi f_2}{f_s}t\right) \\ \vdots \\ \sin\left(\frac{2\pi f_i}{f_s}t\right); \cos\left(\frac{2\pi f_i}{f_s}t\right) \end{bmatrix},$$

where $f_i$ represents a stimulation frequency of the i-th stimulation signal, $f_s$ represents a stimulation frequency of a standard stimulation signal, and t represents a sequence number ranging from 1 to L, I and i both being positive integers, and I being greater than or equal to i;
  fitting, by the processor through the CCA, the first electrooculogram signals to a template signal for electrooculogram signals, wherein the template signal for electroencephalogram signals and the template signal for electrooculogram signals each consists of a sine wave signal and a cosine wave signal;
  extracting, by the processor from the first variable group by using Fourier transform, an electroencephalogram eigenvector for an electroencephalogram signal classification;
  extracting, by the processor from the template signal for electrooculogram signals by using Fourier transform, an electrooculogram eigenvector for an electrooculogram signal classification;
  collecting, by the four electroencephalogram sensors, four channels of electroencephalogram signals in real time, the four channels of electroencephalogram signals being denoted as a second variable group X defined as:

$$X = \begin{bmatrix} channel_1 \\ channel_2 \\ channel_3 \\ channel_4 \end{bmatrix};$$

generating, by the processor based on a first classification result obtained by using the second variable group and the electroencephalogram eigenvector, a first control signal for indicating a target region in the at least two regions;
  generating, by the processor based on a second electrooculogram signal collected by the signal collector in real time and the electrooculogram eigenvector, a second control signal;
  causing, by the processor, the wearable device to perform a moving operation for a character in an application according to the second control signal; and
  causing, by the processor, the wearable device to perform a control operation for the target region in the application according to the first control signal.

10. The signal processing method according to claim 9, wherein the extracting, by the processor from the first variable group by using Fourier transform, an electroencephalogram eigenvector for an electroencephalogram signal classification comprises:
  converting the first variable group into a frequency-domain electroencephalogram signal through the Fourier transform; and extracting an amplitude of fundamental energy of the frequency-domain electroencephalogram signal as the electroencephalogram eigenvector; and wherein the extracting, by the processor from the template signal for electrooculogram signals by using Fourier transform, an electrooculogram eigenvector for an electrooculogram signal classification comprises:

converting the template signal for electrooculogram signals into a frequency-domain electrooculogram signal through the Fourier transform; and extracting an amplitude of fundamental energy of the frequency-domain electrooculogram signal as the electrooculogram eigenvector.

11. A wearable device, comprising: a processor, a memory and a computer program stored on the memory and executable by the processor, wherein the computer program causes the processor to execute steps of the signal processing method according to claim 9.

12. A non-transitory computer-readable storage medium storing computer programs causing the processor to execute steps of the signal processing method according to claim 9.

13. The signal processing method according to claim 9, wherein the electroencephalogram signals are collected from a steady-state visual evoked potential (SSVEP) channel.

14. The signal processing method according to claim 9, wherein the generating, by the processor based on a first classification result obtained by using the second variable group and the electroencephalogram eigenvector, a first control signal for indicating a target region in the at least two regions comprises:

inputting the second variable group and the electroencephalogram eigenvector into a support vector machine (SVM) classification function to obtain the first classification result, wherein the SVM classification function is:

$$f(x) = \text{sgn}\left(\sum_{i=1}^{N} a_i y_i K(x_i, x) + b\right),$$

wherein $K(x_i, x)$ is a kernel function, $a_i$ and $y_i$ are Lagrangian multipliers, and b is an intercept of a regression analysis; and the first classification result is determined based on whether an output value of the SVM classification function is equal to 1.

15. The signal processing method according to claim 14, wherein the at least one electrooculogram sensor consists of four electrooculogram sensors, the four electrooculogram sensors are two horizontal sensors, each of which is configured to collect a signal of a horizontal movement of an eyeball, and two vertical sensors, each of which is configured to collect a signal of a vertical movement of the eyeball; the preset operation corresponding to electrooculogram signals comprises moving an eyeball by the user in different moving directions, the second electrooculogram signal is four channels of electrooculogram signals collected by the four electrooculogram sensors, and the four channels of electrooculogram signals are denoted as a third variable group X1 defined as:

$$X1 = \begin{bmatrix} channel_1 \\ channel_2 \\ channel_3 \\ channel_4 \end{bmatrix};$$

wherein the generating, by the processor based on a second electrooculogram signal collected by the signal collector in real time and the electrooculogram eigenvector, a second control signal comprises:

generating the second control signal based on a second classification result obtained by using the third variable group and the electrooculogram eigenvector, the second control signal indicates a target moving direction in the different moving directions.

16. The signal processing method according to claim 15, wherein the generating the second control signal based on a second classification result obtained by using the third variable group and the electrooculogram eigenvector comprises:

inputting the third variable group and the electrooculogram eigenvector into a support vector machine (SVM) classification function to obtain the second classification result, wherein the SVM classification function is:

$$f(x) = \text{sgn}\left(\sum_{i=1}^{N} a_i y_i K(x_i, x) + b\right),$$

wherein $K(x_i, x)$ is a kernel function, $a_i$ and $y_i$ are Lagrangian multipliers, and b is an intercept of a regression analysis; and the second classification result is determined based on whether an output value of the SVM classification function is equal to 1.

17. The signal processing method according to claim 9, wherein each of the stimulation signals has a frequency not lower than 4 Hz.

18. A signal processing method, performed by a wearable device, the wearable device being an augmented reality (AR) device or a virtual reality (VR) device comprising a processor, a signal collector electrically connected to the processor, and a stimulation generator configured to provide a stimulation signal, the stimulation generator comprising a display panel capable of displaying at different regions with different flicker frequencies to trigger a generation of different electroencephalogram signals, the method comprising:

collecting, by four electroencephalogram sensors of the signal collector, first electroencephalogram signals while a preset operation corresponding to electroencephalogram signals is being executed, wherein the four electroencephalogram sensors consist of an O1 sensor, an O2 sensor, an Oz sensor, and a Pz sensor;

collecting, by four electrooculogram sensors of the signal collector, first electrooculogram signals while a preset operation corresponding to electrooculogram signals is being executed, wherein the four electrooculogram sensors consist of two horizontal sensors, each of which is configured to collect a signal of a horizontal movement of an eyeball, and two vertical sensors, each of which is configured to collect a signal of a vertical movement of the eyeball, wherein the preset operation corresponding to electroencephalogram signals comprises observing at least two regions with different flicker frequencies on the display panel by a user, such that I stimulation signals are provided, and the preset operation corresponding to electrooculogram signals comprises moving an eyeball by the user in different moving directions;

fitting, by the processor through canonical correlation analysis (CCA), the first electroencephalogram signals to a template signal for electroencephalogram signals which is denoted as a first variable group Y defined as:

$$Y = \begin{bmatrix} \sin\left(\frac{2\pi f_1}{f_s}t\right); \cos\left(\frac{2\pi f_1}{f_s}t\right) \\ \sin\left(\frac{2\pi f_2}{f_s}t\right); \cos\left(\frac{2\pi f_2}{f_s}t\right) \\ \vdots \\ \sin\left(\frac{2\pi f_i}{f_s}t\right); \cos\left(\frac{2\pi f_i}{f_s}t\right) \end{bmatrix},$$

where $f_i$ represents a stimulation frequency of the i-th stimulation signal, $f_s$ represents a stimulation frequency of a standard stimulation signal, and t represents a sequence number ranging from 1 to L, I and i both being positive integers, and I being greater than or equal to i;

fitting, by the processor through the CCA, the first electrooculogram signals to a template signal for electrooculogram signals, wherein the template signal for electroencephalogram signals and the template signal for electrooculogram signals each consists of a sine wave signal and a cosine wave signal;

extracting, by the processor from the first variable group by using Fourier transform, an electroencephalogram eigenvector for an electroencephalogram signal classification;

extracting, by the processor from the template signal for electrooculogram signals by using Fourier transform, an electrooculogram eigenvector for an electrooculogram signal classification;

collecting, by the four electroencephalogram sensors, four channels of electroencephalogram signals in real time, the four channels of electroencephalogram signals being denoted as a second variable group X defined as:

$$X = \begin{bmatrix} channel_1 \\ channel_2 \\ channel_3 \\ channel_4 \end{bmatrix};$$

collecting, by the four electrooculogram sensors, four channels of electrooculogram signals in real time, the four channels of electrooculogram signals being denoted as a third variable group X1 defined as:

$$X1 = \begin{bmatrix} channel_1 \\ channel_2 \\ channel_3 \\ channel_4 \end{bmatrix};$$

inputting, by the processor, the second variable group and the electroencephalogram eigenvector into a support vector machine (SVM) classification function to obtain a first classification result;

inputting, by the processor, the third variable group and the electrooculogram eigenvector into the SVM classification function to obtain a second classification result, wherein the SVM classification function is:

$$f(x) = \text{sgn}\left(\sum_{i=1}^{N} a_i y_i K(x_i, x) + b\right),$$

wherein $K(x_i, x)$ is a kernel function, $a_i$ and $y_i$ are Lagrangian multipliers, and b is an intercept of a regression analysis; and the first and second classification results are determined based on whether an output value of the SVM classification function is equal to 1;

generating, by the processor based on the first classification result, a first control signal for indicating a target region in the at least two regions;

generating, by the processor based on the second classification result, a second control signal for indicating a target moving direction in the different moving directions;

causing, by the processor, the wearable device to move a character in an application in the target moving direction according to the second control signal; and causing, by the processor, the wearable device to perform a control operation for the target region in the application according to the first control signal.

* * * * *